(12) United States Patent
Baumfalk et al.

(10) Patent No.: US 8,580,199 B2
(45) Date of Patent: Nov. 12, 2013

(54) OXYGEN SENSOR AND MEASURING METHOD

(75) Inventors: Reinhard Baumfalk, Göttingen (DE); Oscar-Werner Reif, Hanover (DE); Thomas Scheper, Hanover (DE); Michael Fritzsche, Burgdorf (DE)

(73) Assignee: Sartorius Stedim Biotech GmbH (DE)

( * ) Notice: Subject to any disclaimer, the term of this patent is extended or adjusted under 35 U.S.C. 154(b) by 304 days.

(21) Appl. No.: 11/651,823

(22) Filed: Jan. 10, 2007

(65) Prior Publication Data

US 2007/0160500 A1 Jul. 12, 2007

(30) Foreign Application Priority Data

Jan. 11, 2006 (DE) .................. 10 2006 001 642

(51) Int. Cl.
*G01N 21/64* (2006.01)
*G01N 21/76* (2006.01)
*G01J 1/04* (2006.01)
*G02B 6/00* (2006.01)

(52) U.S. Cl.
USPC ............. 422/82.07; 422/82.05; 422/82.11; 422/83; 385/12; 385/129; 436/164; 436/172; 250/227.11; 250/227.23; 250/458.1

(58) Field of Classification Search
None
See application file for complete search history.

(56) References Cited

U.S. PATENT DOCUMENTS

| | | | |
|---|---|---|---|
| 3,612,866 A | 10/1971 | Stevens | |
| 4,849,172 A * | 7/1989 | Yafuso et al. | 422/55 |
| 4,954,318 A * | 9/1990 | Yafuso et al. | 422/59 |
| 5,152,287 A | 10/1992 | Kane | |
| 5,311,013 A * | 5/1994 | Gutcheck et al. | 250/227.23 |
| 5,900,215 A * | 5/1999 | Seifert et al. | 422/82.07 |
| 6,254,829 B1 | 7/2001 | Hartmann et al. | |
| 2001/0001642 A1 | 5/2001 | Klimant et al. | |
| 2002/0029003 A1* | 3/2002 | Mace et al. | 600/532 |
| 2002/0173040 A1* | 11/2002 | Potyrailo et al. | 436/2 |
| 2002/0173922 A1* | 11/2002 | Potyrailo | 702/39 |
| 2004/0166024 A1 | 8/2004 | Klimant | |

FOREIGN PATENT DOCUMENTS

| | | |
|---|---|---|
| DE | 195 48 922 A1 | 7/1997 |
| EP | 0 907 074 A2 | 4/1999 |
| EP | 0 705 897 B1 | 5/1999 |
| GB | 2 132 348 A | 7/1984 |
| WO | WO 02/054076 A2 | 7/2002 |
| WO | WO 02/056023 A1 | 7/2002 |

* cited by examiner

*Primary Examiner* — Neil N Turk
(74) *Attorney, Agent, or Firm* — Gerald E. Hespos; Michael J. Porco; Matthew T. Hespos

(57) ABSTRACT

A sensor for measuring an oxygen content in a liquid or gaseous sample has first and second sensor sections (14*a*, 14*b*). The first sensor section (14*a*) can be brought into contact with the sample and has a luminescent indicator dye embedded in an oxygen-permeable first polymer matrix. The second sensor section (14*b*) is arranged adjacent to the first sensor section (14*a*) and includes the same dye embedded in an oxygen-impermeable second polymer matrix. A light guide (10) guides luminescence excitation light from a light source (31, 32) to the sensor sections (14*a*, 14*b*) and guides luminescence emission light from the sensor section (14*a*, 14*b*) to a detector (39).

18 Claims, 3 Drawing Sheets

OXYGEN SENSOR AND MEASURING METHOD

BACKGROUND OF THE INVENTION

1. Field of the invention

The invention relates to a sensor for measuring an oxygen content in a liquid or gaseous sample, comprising
 a first sensor section that can be brought into contact with the sample and has a luminescent indicator dye embedded in an oxygen-permeable, first polymer matrix,
 light guiding means for guiding luminescence excitation light from a light source to the first sensor section, and
 light guiding means for guiding luminescence emission light from the first sensor section to a detector.

2. Description of the related art

WO 02/103334 A1 discloses an oxygen sensor of the generic type.

It is known about many luminescent dyes, in particular from the group of Pt(II)porphyrins, that their luminescence intensity depends strongly on the oxygen concentration of the medium surrounding the dye. This effect is based on an interaction of the oxygen with the state of the dye molecules energetically excited by excitation light of suitable wavelength. In addition to the luminescence-producing transition from the excited state to the ground state, this interaction can result in an additional radiation free deexcitation path. The probability of this radiation free transition increases with the oxygen concentration. This is called luminescent extinction or quenching by oxygen.

The known sensor utilizes this quenching effect to determine the oxygen content of a sample. Thus, the first sensor section is irradiated with excitation light of suitable wavelength, and the intensity of the luminescence emitted by the indicator dye is measured. Suitable light sources such as, for example, LEDs, and suitable detectors such as, for example, photomultipliers with suitable, upstream filters, are known to the person skilled in the art.

WO 02/103334 A1 addresses as a problem of such a measuring arrangement the dependence of the luminescence intensity not only on the oxygen concentration, but also on fluctuations in the intensity of the excitation light, for example owing to fluctuations in the light source. It is proposed to solve this problem by using a second, oxygen-insensitive dye whose luminescence intensity is determined in the course of a second simultaneous luminescence measurement at the same excitation wavelength and at a separate detection wavelength optimized for the reference dye, and whose ratio with the luminescence intensity value of the indicator dye is formed.

It is disadvantageous with the known sensor that a further, strong dependence, specifically dependence on the temperature of the sensor, that is to say substantially of the sample surrounding the latter, is not taken into account. In addition, the use of a second dye for generating a reference signal entails the disadvantage that said dye can be influenced in a different way from the actual indicator dye by changes in the measuring conditions or by fading.

It is the object of the present invention to make available an oxygen sensor with the aid of which the influences of the temperature on the measuring result can be compensated, and which has no need of a second dye for referencing.

SUMMARY OF THE INVENTION

This object is achieved in conjunction with the features of the invention in which a sensor for measuring an oxygen content in a liquid or gaseous sample includes a first sensor section and light guiding means by virtue of the fact that arranged adjacent to the first sensor section is a second sensor section that includes the same dye, embedded in an oxygen-impermeable, second polymer matrix.

The basic idea of the subject invention is that instead of using a foreign reference dye with a different luminescence characteristic than the indicator dye, the indicator dye itself can be used for the internal referencing, and that by special selection of the polymer matrix a dependence of the latter's luminescence characteristic on the oxygen content of the sample is excluded. This is achieved by selecting a polymer matrix which, in contrast to the polymer matrix of the first sensor section, is impervious to oxygen. In this way, after excitation of the dye in the two sensor sections with a suitable wavelength the sensor supplies a luminescence signal composed of an oxygen-dependent and an oxygen-independent component.

A result value which is independent of the temperature of the sample is obtained by using such a sensor to carry out two measurements at different spectral settings, that is, different excitation and/or detection wavelengths for which the indicator dye has different sensitivities to temperature and oxygen, and offsetting the obtained luminescence intensity values with one another in a suitable way.

There are various possible procedures for acquiring the pairs of intensity measurements which are required in the course of an oxygen measurement. Thus, for example, a first intensity value can be recorded by using a narrowband illumination light to illuminate the sensor sections in the region about an absorption maximum of the indicator dye. The measurement is performed in a narrowband spectral region about an assigned emission maximum of the dye. The second luminescence intensity value is measured after excitation in another, narrowband region about a second absorption maximum of the dye, the detection being performed in a narrowband region about an assigned, second emission maximum. Alternatively, a high energy excitation light can be used for excitation in two individual measurements, and the emission can take place in two separate detection regions, preferably in the region about a separate emission maximum in each case. Finally, it is also possible to carry out the individual measurements with excitation in different excitation spectral regions, preferably in the region about separate absorption maxima of the indicator dye, the detection being performed for the two individual measurements in a common detection spectral region. It has proved to be particularly favorable in this case to select the detection spectral region to be so wide that the emission maxima, which are assigned to the absorption maxima used, are both contained in the implemented, coherent detection region.

Pt(II) octaethylporphyrin, PtOEP for short, has proved to be a particularly advantageous indicator dye. PtOEP firstly has a strong oxygen dependence, and secondly has a good temperature dependence. It is striking here that the dependences of the individual parameters can turn out differently in different spectral regions of the dye, and so a suitable offsetting of luminescence intensities recorded in different spectral regions permits the temperature influence on the oxygen dependence to be "computed away". It has proved to be particularly favorable to offset two luminescence intensity values which have been measured in a detection spectral region between 550 and 650 nm, an excitation wavelength in the region of 530 nm having been used for the first measurement, and an excitation wavelength in the region of 415 nm having been used for the second measurement.

In an advantageous embodiment of the invention, the first, oxygen-permeable polymer matrix is formed from polysulfone (PSU), or polyether sulfone. A particularly strong oxygen dependence of the luminescence of PtOEP has emerged with this selection. This is particularly pronounced when the weight ratio of PtOEP to the polymer of the first matrix lies in the region between 1:1000 and 5:1000, preferably at approximately 2.5:1000.

Epoxy resin has proved to be particularly favorable as an oxygen-impermeable second polymer matrix. Said epoxy resin has an oxygen permeability which is so low that the second sensor section supplies a virtually exclusively temperature dependent signal component. A weight ratio of PtOEP to the polymer of the second matrix in the range between 5:1000 and 50:1000, preferably of approximately 10:1000 has proved to be particularly temperature sensitive.

It is advantageous to design the oxygen-permeable, first polymer matrix as a porous membrane in order to achieve a particularly high signal strength. The design as porous membrane ensures surface maximization, and so a particularly strong interaction can take place between the sample oxygen and the indicator dye embedded in the matrix. The response time of the sensor can thereby be kept very short.

In an advantageous embodiment of the sensor according to the invention, the first sensor section and the second sensor section are arranged one above another in layers, the first sensor section being upstream of the second sensor section of the sample. This ensures that the two sensor sections are exposed to virtually identical optical conditions, the oxygen sensitive sensor section exhibiting a maximum contact surface with the sample. The temperature sensitive sensor section, by contrast, which requires no direct contact with the sample, is protected against possible harmful influences by the first sensor section.

The sensor sections are advantageously applied to the end face and/or the cladding, preferably in the vicinity of the distal end, of a light guide or of a light guide bundle. The light guide or the light guide bundle can transport excitation light in an uncomplicated way toward the sensor sections, and emission light from the sensor sections to the detector. The arrangement in the region of the end face is particularly advantageous with reference to the light intensity which can be used. The arrangement on the cladding in the vicinity of the distal end utilizes the weaker, so-called venescent field of the excitation light, it being possible, particularly when use is made of individual light guides, to implement sensor sections with a substantially greater surface by comparison with the arrangement on the end face.

It is particularly advantageous to provide a lens which is coupled to a light guide input and on whose surface the two sensor sections are arranged, and which couples onto the fiber input luminescent light emitted by the indicator dye. The lens optimizes the optical efficiency of the sensor and simultaneously offers the possibility of enlarging the surface of the sensor sections. This embodiment is particularly advantageous when the fiber input is a constituent of an light guide connector whose output to the input of a light guide connection can be coupled to the light source and the detector. This produces a robust and easily manipulated sensor module which can, for example, easily be installed in the walls of a reaction vessel. The required coupling to a light source and a detector can then be fashioned simply and reversibly with the aid of conventional connector technology. For example, it is possible to use a V-shaped light guide whose first end can be connected to the light source and whose second end can be connected to the detector.

All known types of light sources are suitable as light source. LEDs with suitable upstream optical filters have proved to be particularly advantageous, because they are inexpensive. Photomultipliers with suitable, upstream optical filters can be used, in particular, as detector. Of course, any other type of optical detector can also be used. Particularly in the case of simultaneous measurement at a number of sensors, an imaging optical detector such as, for example, a CCD detector is suitable.

Further features and advantages of the invention result from the following, special description and the drawings which are designed for the purpose of illustration only and not as a definition of the limits of the invention.

DETAILED DESCRIPTION OF THE PREFERRED EMBODIMENTS

Figure 1:
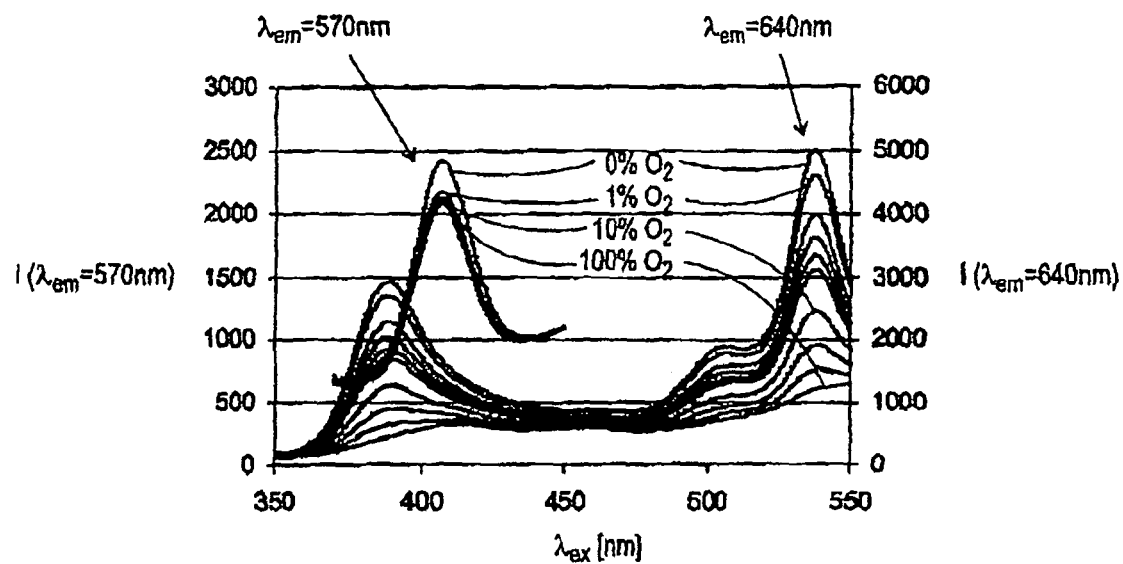
FIG. 1 shows excitation spectra of PtOEP, embedded in a PSU matrix, for various oxygen concentrations.

FIG. 1 shows a number of excitation spectra of platinum (II)octaethylporphyrin, PtOEP for short, embedded in a matrix made from polysulfone, PSU, which were recorded at detection wavelengths of 570 or 640 nm and for different oxygen concentrations of a sample in contact with the PSU matrix. For the sake of clarity, the assigned oxygen value is designated on only a few of the illustrated curves. The strong dependence of the excitation efficiency on the given oxygen concentration is clearly to be recognized. Likewise to be recognized in FIG. 1 is the fact that the oxygen dependence of the luminescence clearly differs between the spectral groups recorded at detection wavelengths of 570 and 640 nm.

Figure 2:
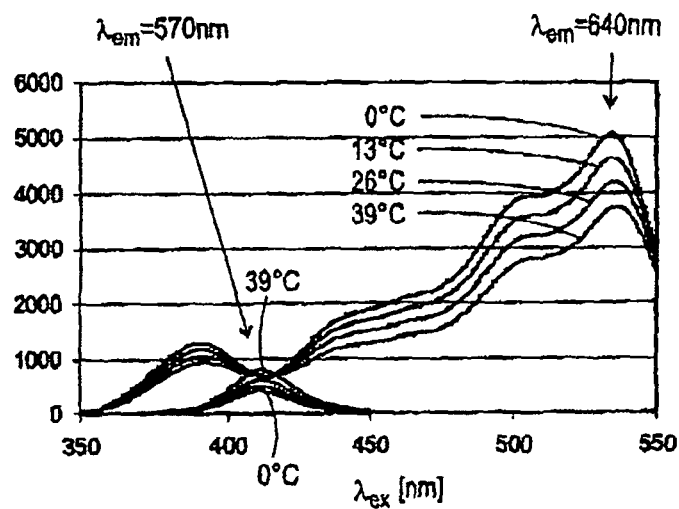
FIG. 2 shows excitation spectra of PtOEP, embedded in an epoxy matrix, for different temperatures.

A similar picture is seen for the temperature dependence of PtOEP. FIG. 2 shows a number of excitation spectra which were recorded on PtOEP, embedded in an epoxy matrix, at detection wavelengths of 570 and 640 nm, and at different temperatures. Clearly to be recognized in FIG. 2 is the strong temperature dependence of the luminescence of PtOEP, and the fact that this dependence differs depending on detection wavelength. In the case of the spectral group recorded at a detection wavelength of 570 nm, for which only two assigned temperature values are plotted in FIG. 2 for the sake of clarity, the temperature dependence of the luminescence intensity behaves exactly inversely to that of the spectral family recorded at a detection wavelength of 640 nm.

The recorded luminescence intensity I is plotted in arbitrary units in both FIGS. 1 and 2. The detection wavelengths are designated in the figures by $\lambda_{em}$, the excitation wavelengths as $\lambda_{ex}$, and displayed in nanometers in each case.

FIGS. 1 and 2 therefore illustrate the dependencies of particularly advantageous embodiments of the sensor sections according to the invention on the oxygen concentration and the temperature, respectively. The temperature dependence of the luminescence characteristic on PtOEP embedded in PSU is not to be recognized in FIGS. 1 and 2. The converse case of an oxygen dependence of PtOEP embedded in epoxy is irrelevant, since the epoxy matrix is virtually opaque for oxygen, and so interaction between oxygen and dye can be neglected. An appropriately constructed sensor section therefore shows exclusively the temperature dependence illustrated in FIG. 2.

Figure 3:
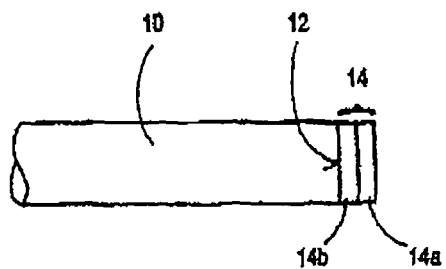
FIG. 3 shows a diagrammatic illustration of an embodiment of the sensor according to the subject invention.

FIG. 3 shows a greatly simplified, diagrammatic illustration of an embodiment of a combination sensor according to the invention. In this embodiment, the sensor carrier is a light guide 10. This can be an individual light guide or a light guide bundle. The active part 14 of the sensor is arranged on the end face 12 of the light guide 10. It comprises two sensor sections 14a, 14b, the first sensor section 14a, which has a maximum contact surface with its surroundings, having the indicator dye, embedded in a polymer matrix permeable to oxygen. The second sensor section 14b, facing the end face 12 of the light guide 10, has the same indicator dye, but the latter is embedded in a polymer matrix impermeable to oxygen. It is preferred for the indicator dye to be PtOEP, for the polymer matrix of the first sensor section 14a to be PSU, and for the polymer matrix of the second sensor section 14b to be epoxy resin.

Two intensity measurements are undertaken during operation of the sensor. In a first measurement, the active region 14 of the sensor is illuminated via the light guide 10 with an excitation light from a first spectral region, which can, for example, be a region with a width of approximately 10 nm about a central wavelength of 530 nm. The resulting luminescence is guided to a detector via the same light guide 10. An intensity measurement is carried out there in a first detection spectral region which, for example, has a width of 10 nm about a central wavelength of 640. The intensity value produced is stored as first luminescence intensity value.

In a second measurement, which can be performed before or after the first measurement, the active region 14 of the sensor is illuminated with a second excitation light from a second excitation spectral region, for example of width 10 nm about a central wavelength of 415 nm. The luminescence produced is fed via the light guide 10 to a detector where a second intensity measurement is undertaken, preferably in a spectral region with an approximate width of 10 nm about a central wavelength of 570 nm. The intensity value produced is stored as second luminescence intensity value.

The two luminescence intensity values are respectively formed by superimposing the luminescences from the first sensor section 14a, which luminesces both in dependence on oxygen and in dependence on temperature, and the second sensor section 14b, which luminesces only in dependence on temperature. A suitable offsetting of the luminescence intensity values with one another leads to a temperature independent result value dependent only on oxygen. Said result value therefore constitutes a temperature independent measure of the oxygen concentration in the sample interacting with the sensor.

The simplest form of offsetting the two luminescence intensity values is the formation of a quotient. However, it can be appropriate to use more complex offsetting schemes. This is dependent on the particular indicator dye used, the particular polymer matrices used and the particular dye concentrations in the respective matrices. However, the person skilled in the art will be able to determine the offsetting methods suitable for his specially selected dye/matrices combination without difficulty on the basis of the technical teaching disclosed here.

In another operating variant of the sensor according to the invention, the outlay on apparatus for recording the two luminescence intensity values can be reduced. In the case of this embodiment, as well, two different measurements are carried out at different excitation wavelengths, as described above. However, the detection is performed in a common detection spectral region which is so wide that it covers the emission maxima respectively assigned to the excitation wavelengths. The common detection spectral region could extend approximately from 550 to 650 nm in the case outlined above.

Figure 4:
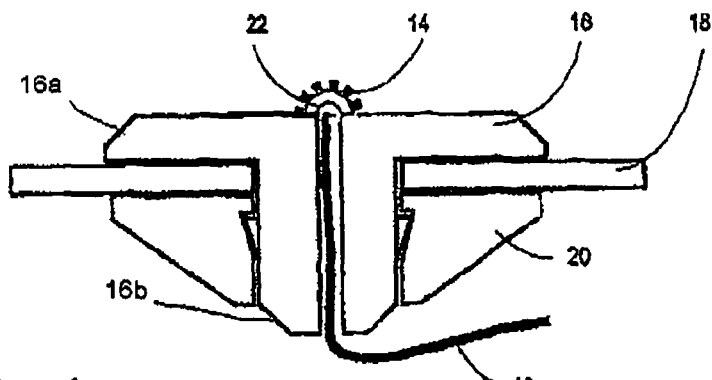
FIG. 4 shows a diagrammatic illustration of a further embodiment of the sensor according to the invention.
Figure 5:
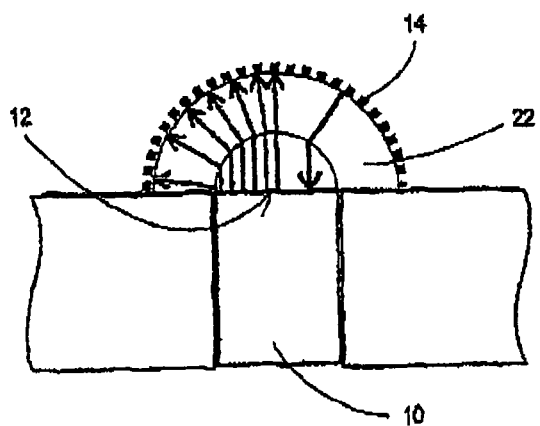
FIG. 5 shows an enlarged illustration of a detail of the lens region of the sensor of FIG. 4.

FIGS. 4 and 5 show a second embodiment of the sensor according to the invention. In this embodiment, the light guide 10 sealingly penetrates a support 16 that has a flange 16a mounted on an inner surface of a container wall 18 and a projection 16b that sealingly penetrates the container wall 18. In the case of the embodiment shown in FIG. 4, the support 16 is latched by a mating piece 20 for fixing on the container wall 18. By contrast with the embodiment of FIG. 3, the active region of the sensor is not applied directly to an end face of the light guide 10. Rather, the light guide 10 is coupled to a lens arrangement 22, which is suitably dimensioned for coupling the luminescent light emitted by the active region 14 of the sensor into the light guide 10. A further task of the lens arrangement 22 is to couple out excitation light brought about by the light guide 10, and to distribute it efficiently over the sensor surface.

Figure 6:
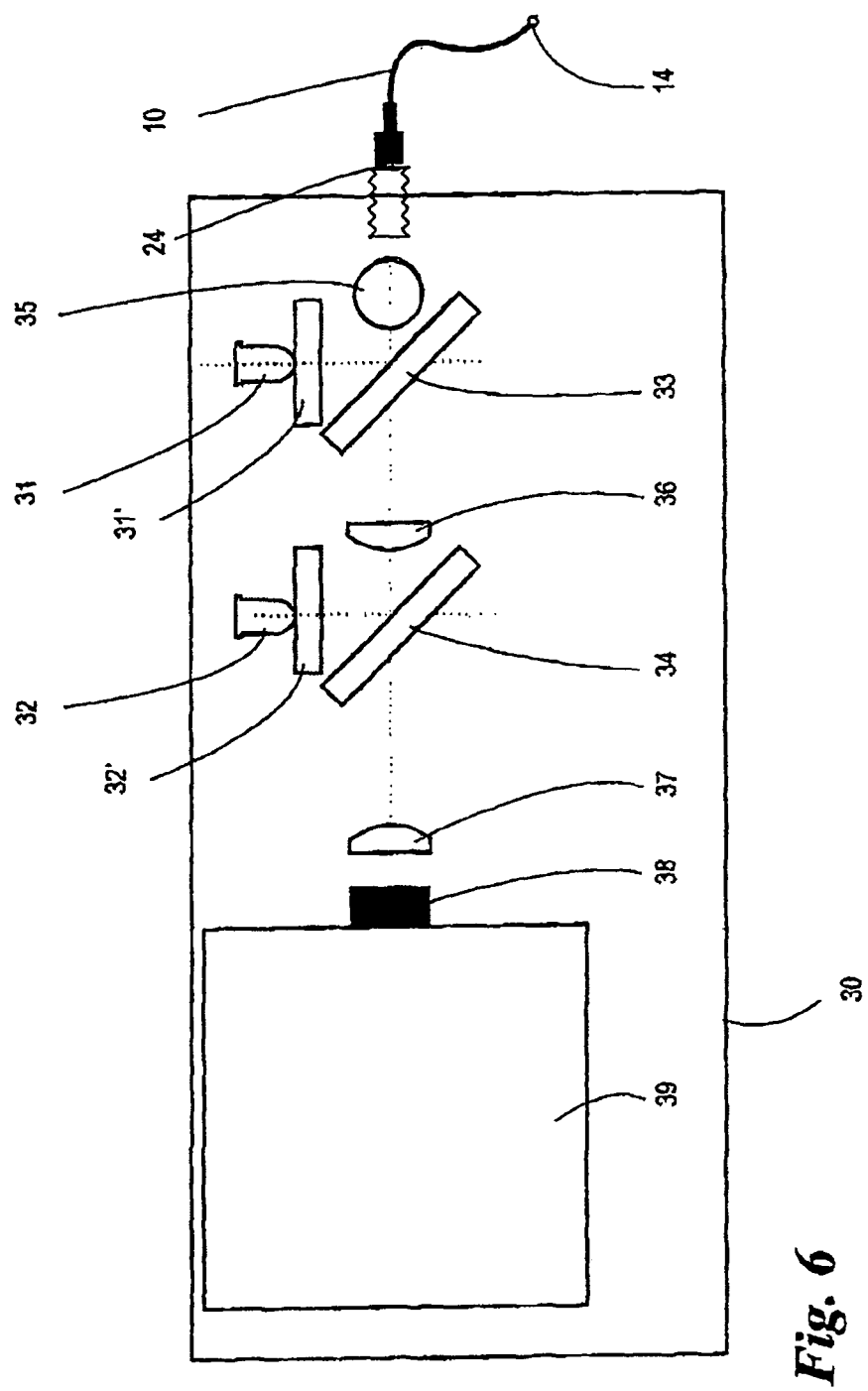
FIG. 6 shows a diagrammatic illustration of a measuring arrangement for use with the sensor according to the invention.

FIG. 6 shows diagrammatically an exemplary embodiment of a measuring arrangement using a sensor according to the invention. The light guide 10 is connected to an optoelectronic structure 30 via a fiber coupler 24, for example an SMA socket. The optoelectronic structure 30 comprises a light source which comprises in the exemplary embodiment shown a green LED 31 with a suitable, upstream filter 31', and a blue LED 32 with a suitable, upstream filter 32'. The light of these LEDs 31, 32 is alternatively coupled via assigned beam splitters 33 and 34, respectively, into the SMA socket 24, and thus into the light guide 10. Coupling lenses 35 and 36 are provided to this end. During detection, the luminescent light along the wavelength is coupled out of the SMA socket 24 by means of the coupling optics 35 and 36, and traverses the color splitters 33 and 34. A further coupling lens 37 couples the luminescent light via a detection filter 38 into a photomultipler 39. More or fewer filters can be used depending on the special optical requirements; the filters can be designed as edge or bandpass filters in accordance with a respective application; automated filter exchangers can also be provided. Again, the light source need not necessarily consist of a number of LEDs, although this constitutes an embodiment which is particularly cost effective. Other light sources known to the person skilled in the art such as, for example, lasers, incandescent lamps or discharge lamps can likewise be used.

Of course, the exemplary embodiments discussed in the detailed description and shown in the figures represent merely exemplary embodiments of the present invention. The technical teaching disclosed here provides the person skilled in the art with the basis for a wide spectrum of variations. Thus, for example, the spatial arrangement of the sensor sections 14a and 14b can deviate from the form illustrated. Again, designing the light guiding means as fiberoptic light guides is not mandatory for the invention. Free beam arrangements can be taken into consideration as an alternative. Again, the selection of the dyes and polymer matrices is not restricted to the exemplary embodiments discussed in detail. Rather, it is also possible to use other dye/polymer combinations which exhibit in principle similar dependencies of their luminescences on the oxygen content and temperature of a sample. Finally, the invention is not restricted to the measurement and offsetting of pairs of luminescence intensity values. Rather, more than two luminescence intensity values can also be recorded for different spectral settings and offset from one another.

What is claimed is:

1. A sensor for measuring oxygen content in a liquid or gaseous sample, comprising a light guiding means having a first end face for receiving luminescence excitation light from a light source and a second end face opposite the first end face, an active region applied to the second end face, the light guiding means being disposed to guide the luminescence excitation light to the active region, and the light guiding means further guides luminescence emission light from the active region to a detector, characterized in that the active region comprises a first sensor section that has an oxygen-sensitive luminescent indicator dye embedded in an oxygen-permeable first polymer matrix and a second sensor section that has said oxygen-sensitive luminescent indicator dye embedded in an oxygen-impermeable second polymer matrix, the second sensor section being disposed between the first sensor section and the second end face of the light guiding means so that the first sensor section can be brought into contact with said sample and so that the light guiding means guides the luminescence excitation light from the light source to the first sensor section via the second sensor section and guides the luminescence emission light from both the first sensor section and the second sensor section via the second end face to the detector, so that the first and second sensor are positioned to be exposed to virtually identical optical conditions with the oxygen-permeable first polymer matrix being exposed to the sample and the oxygen-impermeable second polymer matrix being substantially protected from the sample by the first sensor section and so that the detector receives a luminescence signal composed of an oxygen-dependent component and an oxygen-independent component for measuring oxygen content of the sample independent of temperature.

2. The sensor according to claim 1, characterized in that said oxygen-sensitive luminescent indicator dye is a Pt(II)-porphyrin.

3. The sensor according to claim 1, wherein the first polymer matrix is formed from polysulfone or polyether sulfone.

4. The sensor according to claim 2, characterized in that the weight ratio of said Pt(11)-porphyrin to the polymer of the first matrix is between 1:1000 and 5:1000.

5. The sensor according to claim 2, wherein the second polymer matrix comprises an epoxy resin.

6. The sensor according to claim 5, characterized in that the weight ratio of said Pt(11)-porphyrin to the polymer of the second matrix is between 5:1000 and 50:1000.

7. The sensor according to claim 1, characterized in that the oxygen-permeable, first polymer matrix is a porous membrane.

8. The sensor according to claim 1, characterized in that the first sensor section and the second sensor section are arranged one above another in layers, the first sensor section being upstream of the second sensor section of the sample.

9. The sensor according to claim 1, characterized in that the sensor sections are applied to the second end face and/or a cladding of a light guide or of a light guide bundle.

10. The sensor according to claim 1, wherein a lens arrangement is coupled to a light guide and wherein said lens arrangement comprises an outer surface, said two sensor sections being arranged on the outer surface, and said lens arrangement directs a luminescent light emitted by the indicator dye to said detector.

11. The sensor according to claim 10, characterized in that the fiber input is a constituent of a light guide connector whose output to the input of a light guide connection can be coupled to the light source and the detector.

12. The sensor according to claim 2, wherein said PT(11)-porphyrin is Pt(11)octaethylporphyrin.

13. The sensor according to claim 4, wherein the weight ratio of said Pt(11)-porphyrin to the polymer of the first matrix is approximately 2.5:1000.

14. The sensor according to claim 6, wherein the weight ratio of said Pt(11)-porphyrin to the polymer of the first matrix is approximately 10:1000.

15. A sensor for measuring oxygen content in a liquid or gaseous sample, comprising:
at least one light source for emitting light at selected one or more wavelengths;
a light guide for guiding luminescence excitation light from the light source to an end face of the light guide;
an active region disposed on the end face of the light guide for impingement by light emitted from the end face of the light guide, the active region comprising first and second sensor sections disposed adjacent to one another and so that the second sensor section faces the end face of the light guide, and so that the first sensor section is adjacent to and outwardly of the second sensor section relative to the end face of the light guide so that light emitted from the end face of the light guide impinges on the first sensor section via the second sensor section and so that the first and second sensor sections are exposed to virtually identical optical conditions with an oxygen-permeable first polymer matrix being exposed to the sample and an oxygen-impermeable second polymer matrix being protected from the sample by the first sensor section, the first sensor section comprising an oxygen-sensitive luminescent indicator dye embedded in the oxygen-permeable first polymer matrix, the second sensor section comprising said oxygen-sensitive luminescent indicator dye embedded in the oxygen-impermeable second polymer matrix; and
a detector disposed for being impinged upon by luminescence emission light from the first and second sensor sections, so that the detector receives a luminescence signal composed of an oxygen-dependent component and an oxygen-independent component for measuring oxygen content of the sample independent of temperature.

16. The sensor of claim 15, wherein the second sensor section is arranged on the end face of the light guide and so that the second sensor section is between the end face of the light guide and the first sensor section.

17. The sensor of claim 15, further comprising a lens between the end face of the light guide and the active region, the lens being configured for coupling the luminescence emission light from the first and second sensor sections into the end face of the light guide.

18. The sensor of claim 17, wherein the sensor is configured for measuring oxygen content in a liquid or gaseous sample within a container, the container having a container wall with opposite inner and outer surfaces and an aperture extending through the container wall, the sensor further comprising a support having a flange with a first surface to be mounted on the inner surface of the container wall and a second surface opposite the first surface of the flange, the support further having a projection extending from the flange a distance exceeding a distance between the inner and outer surfaces of the container wall, a mating piece mounted to the projection of the support so that the mating piece is spaced from the flange by a distance substantially corresponding to a distance between the inner and outer surfaces of the container wall, portions of the light guide adjacent the end face thereof sealingly penetrating through the projection and the flange of the support, the lens being disposed on the second surface of the flange of the support so that the active region of the sensor is in the container.

\* \* \* \* \*